US008864789B2

(12) United States Patent
Balgobin et al.

(10) Patent No.: US 8,864,789 B2
(45) Date of Patent: Oct. 21, 2014

(54) INTERVENTIONAL MEDICAL DEVICE SYSTEM HAVING A SPIRAL SECTION AND RADIOPAQUE MARKER AND METHOD OF MAKING THE SAME

(75) Inventors: Keith Balgobin, Pembroke Pines, FL (US); Vladimir Mitelberg, Austin, TX (US); Jason T. Rainer, Miramar, FL (US); John H. Thinnes, Jr., Miami Beach, FL (US)

(73) Assignee: Depuy Synthes Products, LLC, Raynham, MA (US)

( * ) Notice: Subject to any disclaimer, the term of this patent is extended or adjusted under 35 U.S.C. 154(b) by 1087 days.

(21) Appl. No.: 11/741,079

(22) Filed: Apr. 27, 2007

(65) Prior Publication Data

US 2008/0269721 A1 Oct. 30, 2008

(51) Int. Cl.

| A61M 29/00 | (2006.01) |
|---|---|
| A61F 2/962 | (2013.01) |
| A61F 2/88 | (2006.01) |
| A61B 17/12 | (2006.01) |
| A61F 2/966 | (2013.01) |
| A61F 2/95 | (2013.01) |
| A61F 2/30 | (2006.01) |
| A61M 25/01 | (2006.01) |

(52) U.S. Cl.
CPC ............. *A61B 17/12022* (2013.01); *A61F 2/88* (2013.01); *A61B 2017/12054* (2013.01); *A61F 2/966* (2013.01); *A61F 2250/0098* (2013.01); *A61F 2002/9511* (2013.01); *A61B 17/1214* (2013.01); *A61B 17/12113* (2013.01); *A61F 2/962* (2013.01); *A61F 2002/3008* (2013.01); *A61M 25/0105* (2013.01)
USPC ........................................................ 606/200

(58) Field of Classification Search
CPC .... A61B 17/1214–17/12154; A61B 17/12113; A61B 2017/1205–2017/12095
USPC .......... 606/108, 200; 623/1.11, 1.12; 600/585
See application file for complete search history.

(56) References Cited

U.S. PATENT DOCUMENTS

| 5,047,050 | A | * | 9/1991 | Arpesani ...................... 623/1.34 |
|---|---|---|---|---|
| 5,573,520 | A | * | 11/1996 | Schwartz et al. ............. 604/526 |
| 5,814,062 | A | * | 9/1998 | Sepetka et al. ................ 606/198 |
| 5,895,391 | A | * | 4/1999 | Farnholtz ...................... 606/108 |
| 6,059,814 | A | * | 5/2000 | Ladd ............................. 606/200 |

(Continued)

OTHER PUBLICATIONS

U.S. Appl. No. 11/461,231, Jul. 31, 2006, Mitelberg et al.

(Continued)

*Primary Examiner* — Darwin Erezo
*Assistant Examiner* — Jonathan Hollm
(74) *Attorney, Agent, or Firm* — Cook Alex Ltd.

(57) ABSTRACT

A system is provided that includes an elongated introducer navigable through body vessels of a human subject and a pusher component for incorporation within the introducer. The pusher component includes a tubular portion with a spiral ribbon. A radiopaque marker is secured to at least a portion of the spiral ribbon such that an outer surface of the radiopaque marker is substantially flush with an outer surface of the tubular portion immediately proximal and/or immediately distal the radiopaque marker. According to a method of manufacturing such a component, the spiral ribbon is formed by a spiral cutting operation and a pre-assembly radiopaque marker member is crimped onto the spiral ribbon. According to another method of manufacturing such a component, the spiral ribbon is formed by winding a filament and a pre-assembly radiopaque marker member is crimped onto the spiral ribbon.

4 Claims, 2 Drawing Sheets

(56) References Cited

U.S. PATENT DOCUMENTS

| | | | |
|---|---|---|---|
| 6,187,025 B1* | 2/2001 | Machek | 606/200 |
| 6,352,531 B1* | 3/2002 | O'Connor et al. | 606/15 |
| 6,517,547 B1* | 2/2003 | Feeser et al. | 606/108 |
| 6,520,934 B1* | 2/2003 | Lee et al. | 604/103.1 |
| 6,540,721 B1* | 4/2003 | Voyles et al. | 604/103.1 |
| 6,574,497 B1* | 6/2003 | Pacetti | 600/420 |
| 6,612,998 B2* | 9/2003 | Gosiengfiao et al. | 600/585 |
| 2002/0032460 A1* | 3/2002 | Kusleika et al. | 606/200 |
| 2002/0143362 A1* | 10/2002 | Macoviak et al. | 606/200 |
| 2004/0093011 A1* | 5/2004 | Vrba | 606/200 |
| 2005/0004653 A1 | 1/2005 | Gerberding et al. | |
| 2005/0154417 A1* | 7/2005 | Sepetka et al. | 606/200 |
| 2005/0177182 A1* | 8/2005 | van der Burg et al. | 606/157 |
| 2006/0025802 A1* | 2/2006 | Sowers | 606/200 |
| 2006/0100687 A1 | 5/2006 | Fahey et al. | |
| 2006/0212105 A1 | 9/2006 | Dorn et al. | |
| 2006/0258987 A1* | 11/2006 | Lentz et al. | 604/164.01 |
| 2007/0010849 A1 | 1/2007 | Balgobin et al. | |
| 2007/0173862 A1* | 7/2007 | Fernandez et al. | 606/108 |
| 2007/0282370 A1* | 12/2007 | Brady et al. | 606/200 |
| 2009/0036768 A1* | 2/2009 | Seehusen et al. | 600/424 |

OTHER PUBLICATIONS

U.S. Appl. No. 11/461,245, Jul. 31, 2006, Mitelberg et al.

Interface Associates, Marker Band Swager, Continuous Rotation, Apr. 20, 2007, www.interfaceusa.com/Product.aspx?ID=4865.

* cited by examiner

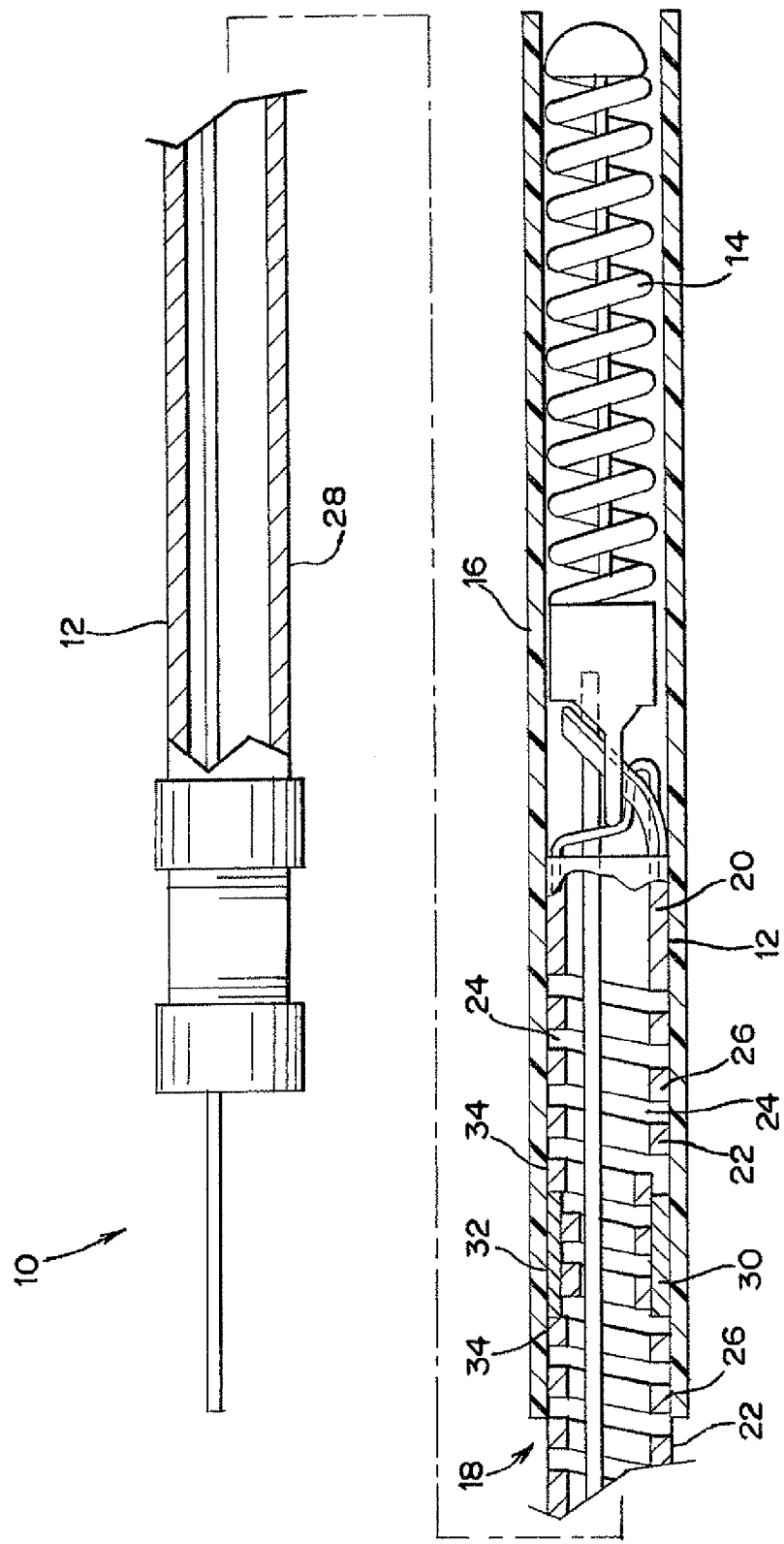

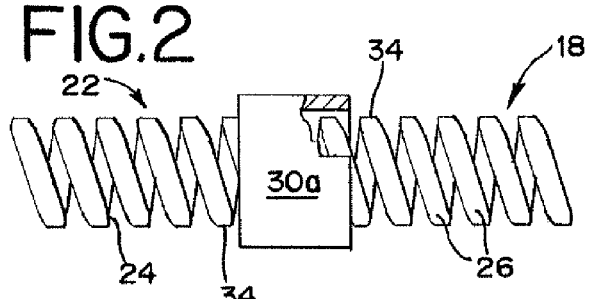
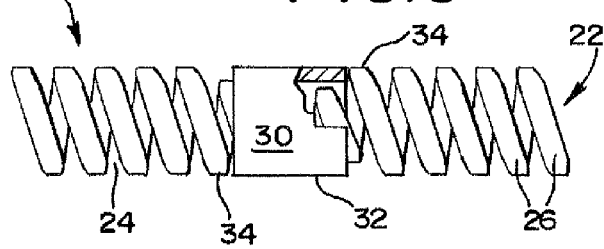
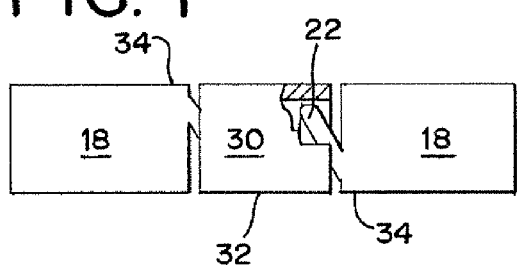
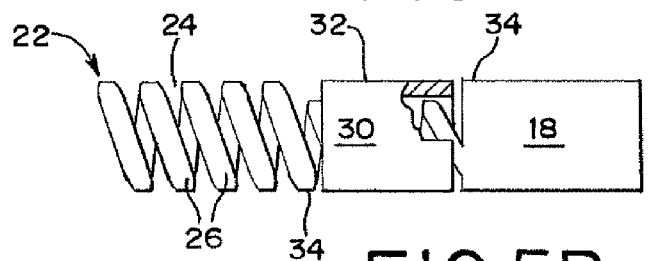
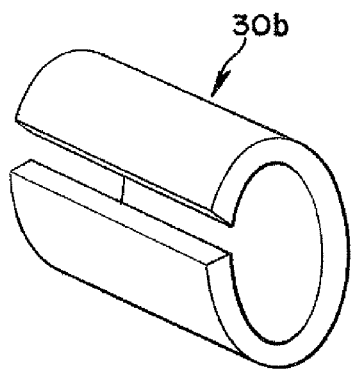
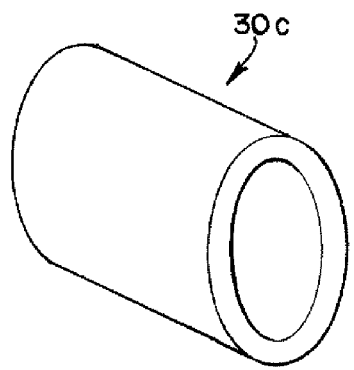

INTERVENTIONAL MEDICAL DEVICE SYSTEM HAVING A SPIRAL SECTION AND RADIOPAQUE MARKER AND METHOD OF MAKING THE SAME

FIELD OF THE INVENTION

This invention generally relates to medical devices that are navigable through body vessels of a human subject. More particularly, this invention relates to tubular devices having a spiral section and radiopaque marker and methods of making the same.

DESCRIPTION OF RELATED ART

A number of medical procedures require the introduction of tubing to a body vessel. For example, vessel defects, such as blockages and stenoses, within the human vasculature system are often treated by the intraluminal delivery of treatment fluids or implants, such as expandable stents and embolic coils. Implants can take any of a number of forms and may be delivered to a diseased site in a number of manners. According to one known method of delivering a medical implant, the distal end of a flexible catheter is positioned adjacent to a target site of a body vessel, such as an aneurysm. Once the catheter is properly positioned, a delivery/detachment system is passed through a lumen of the catheter until a distal end of the delivery system exits the distal end of the catheter in the area of the target site. An implant, such as an embolic coil, carried at the distal end of the delivery/detachment system is thereafter released to the diseased site.

The path to the target site is typically tortuous, so the catheter is preferably relatively flexible to allow it to pass through the vasculature to the desired site. Conversely, the catheter may be required to pass through constricted vessels, so it is also desirable for it to exhibit good column strength. When the catheter has been properly positioned, the delivery system must follow the path defined by the catheter, so the delivery system also preferably has similar characteristics of flexibility and good column strength. In particular, it is generally preferred for the delivery system to exhibit column strength and good pushability, particularly at its proximal end, to allow the delivery system to be pushed through the catheter, and relatively flexible especially at a distal end, to allow the delivery system to follow the path defined by the catheter.

It may also be preferred to provide the catheter and/or the delivery system with one or more radiopaque markers, typically positioned at the distal end thereof, to aid in the positioning and deployment of the implant to a target location within a body vessel. The implant itself may also be provided with a radiopaque marker. Radiopaque markers facilitate the positioning of the implant within a blood vessel by allowing a physician to determine the exact location and orientation of the catheter, delivery system, and/or implant under x-ray or fluoroscopy. These markers are typically formed of a radiopaque material such as tantalum, zirconium, gold, platinum, iridium, tungsten, or a combination thereof.

For a radiopaque marker applied to certain medical device components, an important objective may be to have the marker be substantially flush with an outer surface of the component. For example, as described previously, an implant delivery system is pushed through a catheter to deliver an implant to a target location within a body vessel. If the distal end of the delivery system has a radiopaque marker extending beyond the outer surface of the system, it creates a projecting discontinuity or "ledge," which increases the risk that the projecting marker will promote potentially undesirable contact with a guiding catheter, other component of the system, a body vessel wall or the like. In the case of a marker band that imparts a projecting discontinuity (which can be circumferential in the case of a band that extends the full circumferential extent of the device), there is a potential risk of some adverse effect, no matter how minimal, or of interference with a fully smooth operation of the diagnostic or treatment system, such as by snagging upon a catheter as it is pushed therethrough to the target location. It will be appreciated by those of ordinary skill in the art that other medical device components may similarly benefit from a radiopaque marker that is flush with the outer surface of the component.

A general aspect or object of the present invention is to provide a medical device system that includes a component having a radiopaque marker which avoids the creation of a "ledge" that may adversely affect performance of the component within an introducer or catheter through which the component is administered.

Another aspect or object of this invention is to provide a method of affixing a radiopaque marker to a medical device component so as to avoid the creation of a "ledge" that may adversely affect performance of that component within an introducer or catheter through which the component is administered.

Other aspects, objects and advantages of the present invention, including the various features used in various combinations, will be understood from the following description according to preferred embodiments of the present invention, taken in conjunction with the drawings in which certain specific features are shown.

SUMMARY

In accordance with one embodiment or aspect of the present invention, a component of an interventional medical device system operable while within a body vessel includes an elongated introducer within which is positioned a pusher that is provided with a generally hollow tubular portion. The tubular portion includes a spiral ribbon. An arcuate radiopaque marker overlays at least a portion of the spiral ribbon. An outer surface of the radiopaque member is substantially flush with an outer surface of the tubular portion and/or the spiral ribbon immediately proximal or immediately distal the radiopaque marker.

According to another aspect or embodiment of the present invention, a method of creating a component of an interventional medical device system that includes an elongated introducer and a pusher component therewithin, the system being operable while within a body vessel is provided that includes providing a tubular member and a cutting device. The cutting device is operated to create a helically oriented cut section in the tubular member. A pre-assembly radiopaque marker member then is positioned over at least a portion of the cut section. The radiopaque marker member is crimped onto the cut section such that an outer surface of the thus assembled radiopaque marker is substantially flush with an outer surface of the tubular portion and/or the cut section immediately proximal or immediately distal the radiopaque marker.

According to yet another aspect or embodiment of the present invention, a method of creating a component of an interventional medical device system that includes an elongated introducer and a pusher therewithin, the system being operable while within a body vessel is provided that includes providing a tubular member and an elongated filament. At least a portion of the filament is wound to create a helically wound section. A pre-assembly radiopaque marker member then is positioned over at least a portion of the wound section. The radiopaque marker member is crimped onto the wound section such that the outer surface of the thus formed radiopaque marker is substantially flush with an outer surface of the tubular portion and/or the wound section immediately proximal or immediately distal the radiopaque marker.

Special application for the present invention has been found for tubular portions of medical device guidewires, catheters, microcathers, fine-bore guiding cathers, and embolic coil/implant delivery, detachment or retrieval systems. Suitable medical procedure applications are illustrated in U.S. patent application Ser. Nos. 11/461,231 and 11/461,245 to Mitelberg et al., filed Jul. 31, 2006, which are hereby incorporated herein by reference. However, the present invention is also applicable to tubular components of other devices adapted for movement through body lumens, so it will be understood that certain embodiments of the products and methods described herein are not limited to particular medical devices or particular surgical applications.

BRIEF DESCRIPTION OF THE DRAWINGS

FIG. 1 is partial cross-sectional view of an implantable medical device delivery system incorporating an elongated introducer and a medical device component according to an aspect of the present invention;

FIG. 2 is a side elevational view of a tubular portion of a component according to an aspect of the present invention, associated with a pre-assembly radiopaque marker member in a disconnected condition, a portion of the pre-assembly radiopaque marker member being broken away for clarity;

FIG. 3 illustrates the tubular portion and radiopaque marker of FIG. 2, with the radiopaque marker in a connected condition, a portion of the radiopaque marker being broken away for clarity;

FIG. 4 is a side elevational view of another embodiment of a tubular portion of a medical device component and associated radiopaque marker, a portion of the radiopaque marker being broken away for clarity;

FIG. 5A is a front perspective view of an embodiment of a pre-assembly radiopaque marker member according to an aspect of the present invention;

FIG. 5B is a front perspective view of another embodiment of a pre-assembly radiopaque marker member according to an aspect of the present invention; and FIG. 6 is a side elevational view of yet another embodiment of a tubular portion of a medical device component and associated radiopaque marker, a portion of the radiopaque marker being broken away for clarity.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 shows an interventional medical device system 10 operable while within a body vessel. The illustrated system 10 is an embolic coil delivery system and operates generally according to the description found in U.S. Patent Application Publication No. 2007/0010849 to Balgobin et al., which is hereby incorporated herein by reference. The illustrated system 10 is merely exemplary of an interventional medical device in which a medical device component according to the present invention may be incorporated and other devices may be employed without departing from the scope of the present invention.

The system 10 includes a pusher member 12, which is an exemplary medical device component according to the present invention. The pusher member 12 is a generally hollow tube or tubular structure used to push an embolic coil 14 through an introducer or catheter 16 of the system 10. When used herein, the terms "tubular" and "tube" are to be construed broadly and are not limited to a structure that is a right cylinder or strictly circumferential in cross-section or of a uniform cross-section throughout its length. For example, the pusher member 12 is shown as a substantially right cylindrical structure. However, the pusher member 12 may have a tapered or curved outer surface without departing from the scope of the present invention.

The pusher member 12 includes a generally hollow tubular portion 18, illustrated in FIG. 1 at a distal end 20 thereof, with a spiral ribbon 22. The spiral ribbon 22 comprises a helical cut, opening, or separation 24 defining a plurality of adjacent turns 26. Typically, it is preferred for at least the proximal end 28 of the pusher member 12 to exhibit good column strength, so the pusher member 12 may comprise a metal hypotube, with the proximal end 28 being a non-spiral section. When a medical device component according to the present invention is provided as a metal tube, the spiral ribbon 22 may comprise a spiral cut portion thereof. A spiral ribbon so formed is alternatively referred to herein as a "cut section" of the tubular portion.

According to one method of forming the cut section, a generally hollow tubular member and a cutting device are provided. The nature of the cutting device depends on the material of the hollow tubular member, but a laser is a suitable cutting device for use with a metallic tubular member, such as a hypotube. In the case of a stainless steel tubular member suitable for use in delivering a neurovascular implant, i.e. a tubular member having an outer diameter no greater than 0.025 inch, the laser may be adapted to provide a kerf in the range of about 0.0005-0.0015 inch (preferably 0.001 inch). The cutting device is operated to create a cut in the tubular member. At least one of the tubular member and the cutting device is moved in a substantially helical path with respect to the other to form a helical cut in the tubular member.

The helical movement of the above method may be accomplished in a variety of ways, such as by rotating the cutting device about the tubular member or by fixing the cutting device and rotating the tubular member on a mandrel. The helical movement may also be achieved by moving both the tubular member and the cutting device, such as by rotating the tubular member while moving the cutting device axially with respect to the rotating tubular member.

In another embodiment, the spiral ribbon of a component according to the present invention may be formed by a winding operation. In such a method, at least a portion of an elongated filament, such as a metallic flat ribbon wire, is wound so as to assume a generally hollow tubular shape. It may be preferred to wind the filament in a helical direction about a substantially cylindrical structure, such as a mandrel, to improve the resulting shape of the spiral ribbon. A spiral ribbon so formed is alternatively referred to herein as a "wound section" of the tubular portion.

As shown in FIG. 1, the spiral ribbon 22 is associated with a radiopaque marker 30. The radiopaque marker 30 may be comprised of any radiopaque material, including but not limited to tantalum, zirconium, gold, platinum, iridium, tungsten, or a combination thereof. The radiopaque marker 30 overlays at least a portion of the spiral ribbon 22. The radiopaque marker 30, in a connected condition shown in FIG. 1 and described in greater detail herein, may be shorter than the spiral ribbon 22 in a direction along the length of the medical device component, in which case the radiopaque marker 30 will overlay a portion of the spiral ribbon 22 less than the total length of the spiral ribbon 22 (FIGS. 1 and 3). Alternatively, the radiopaque marker 30, when in a connected condition, may have a length substantially the same as that of the spiral ribbon 22, in which case the radiopaque marker 30 will overlay a portion of the spiral ribbon 22 corresponding generally to the entire length of the spiral portion 22 (FIG. 4).

The radiopaque marker originates as a pre-assembly radiopaque marker member 30a, which is movable or transformable from a disconnected or pre-assembly condition, shown generally in FIG. 2, to a connected or assembled or fully assembled condition, shown generally in FIGS. 1, 3 and 4. In the disconnected or pre-assembly condition, the pre-assembly radiopaque marker member 30a is placed against the outer surface of the spiral ribbon 22, but the pre-assembly radiopaque marker member 30a will not be fixedly secured to the spiral ribbon 22 or any portion thereof. When the pre-assembly radiopaque marker member 30a is moved to the connected condition of FIGS. 1, 3 and 4, it clamps down on one or more turns 26 of the spiral ribbon 22 as an assembled radiopaque marker 30 and will be substantially affixed to at least a portion of the spiral ribbon 22.

Preferably, a pre-assembly radiopaque marker member 30a, which is in a disconnected condition, is positioned over at least a portion of the spiral ribbon 22 (FIG. 2) and then moved to the connected condition (FIG. 3) by a crimping operation. In one embodiment, the pre-assembly radiopaque marker member may be initially provided as a generally flat sheet or a C-shaped sheet of radiopaque material, generally designated at 30b in FIG. 5A, that is placed over a portion of the spiral ribbon 22 and crimped therearound so as to overlay it and be fixedly secured thereto as an assembled radiopaque marker 30. A radiopaque marker 30 so secured to the spiral ribbon 22 may be substantially arcuate, typically defining an arc greater than 180° to ensure that the radiopaque marker 30 remains secured to the spiral ribbon 22. More typically, the radiopaque marker 30 may define an arc substantially greater than 180° when secured to the spiral ribbon 22, for example in the range of approximately 300° to approximately 330°, for improved visualization when the interventional medical device 10 is within a body vessel. Most advantageously, the sheet 30b is adapted such that it will be substantially tubular, preferably without overlapping edges, and substantially encircle at least a portion of the spiral ribbon 22 as a radiopaque marker 30 in the connected condition. A radiopaque marker having a tubular configuration may be advantageous because such a radiopaque marker is viewable under x-ray or fluoroscopy regardless of the position of the component in a body vessel.

In one embodiment, illustrated in FIG. 5B, a pre-assembly radiopaque marker member 30c is initially provided in a substantially tubular configuration and substantially encircles at least a portion of the spiral ribbon 22 when subsequently moved to the connected condition. When used herein, the term "arcuate" applies to both partially tubular radiopaque markers (i.e., those defining an arc less than 360° when secured to the spiral ribbon) and tubular radiopaque markers (i.e., those defining a 360° arc when secured to the spiral ribbon). A radiopaque marker initially provided as a pre-assembly marker member 30c according to the configuration of FIG. 5B may be advantageous because the crimping operation may be carried out automatically by a swaging machine according to known design. One exemplary swaging machine which is suitable for use with a substantially tubular pre-assembly radiopaque marker member 30c is the model MBS-140CR marker band swager from Interface Associates of Laguna Niguel, Calif.

As shown in FIGS. 1, 3 and 4, the radiopaque marker 30 will radially compress the portion of the spiral ribbon 22 which it overlays. Advantageously, the radiopaque marker 30 will compress the spiral ribbon 22 to the extent that the outer surface 32 of the radiopaque member 30 is substantially flush with the outer surface 34 of the tubular portion 18 immediately proximal or immediately distal the radiopaque marker 30. More typically, the outer surface 32 of the radiopaque marker 30 is substantially flush with the outer surface 34 of the tubular portion 18 immediately proximal and immediately distal the radiopaque marker 30, as shown in FIGS. 1, 3 and 4. If the spiral ribbon 22 is longer than the radiopaque marker 30, this "outer surface of the tubular portion" will correspond to the outer surface of the spiral ribbon 22 of the tubular portion 18 (FIGS. 1 and 3). If the spiral ribbon 22 is substantially the same length as the radiopaque marker 30, the "outer surface of the tubular portion" may instead correspond to a non-spiral section of the tubular portion 18 (FIG. 4). In yet another embodiment, illustrated in FIG. 6, the radiopaque marker 30 may be positioned such that it is substantially flush on one end with the spiral ribbon 22 of the tubular portion 18 and substantially flush with a non-spiral section of the tubular portion 18 on the other end.

When the ends of the radiopaque marker 30 are substantially flush with the sections of the tubular portion 18 immediately adjacent thereto, there will be no regions of projecting discontinuity or "ledges" created. If the component is a pusher member of an embolic coil delivery/detachment system, as shown in FIG. 1, the lack of "ledges" promotes smooth movement of the device through a catheter or introducer. Other advantages may also be achieved by such a configuration, depending upon the nature of the interventional medical device and the anticipated use thereof.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An interventional medical device system operable while within a body vessel, comprising:
  an elongated introducer having a lumen, said introducer being adapted for administration within a body vessel to deliver an embolic coil;
  a pusher component positioned for slidable movement within said lumen of the elongated introducer, said pusher component being a hypotube having a distal end portion to which a proximal end of the embolic coil is detachably attached and including a generally hollow metallic tubular portion and a spiral ribbon length having a plurality of separations defining a plurality of adjacent turns;
  said spiral ribbon length has an outer surface and is spaced proximally from said distal end portion by a non-spiral distal section of the tubular portion, the spiral ribbon length is spaced distally from the remainder of the pusher component being a non-spiral proximal section of the tubular portion, both the non-spiral distal section and the non-spiral proximal section comprise the hypotube without any cut section;

an arcuate radiopaque marker having an outer surface and an inner surface, said radiopaque marker overlaying and fixedly secured to said outer surface of the spiral ribbon length, said radiopaque marker being in a connected condition at which the marker inner surface engages the spiral ribbon outer surface and the marker is clamped down on and radially compressed onto the spiral ribbon length to define a radially compressed spiral ribbon length;

said outer surface of the radiopaque marker as thus assembled at its said connected condition onto the radially compressed ribbon length outer surface is dimensionally reduced from a pre-assembly radiopaque marker member that is dimensionally larger than said marker outer surface as thus assembled onto the spiral ribbon, and the marker at its connected condition is substantially flush with an outer surface of each of the non-spiral proximal section and the non-spiral distal section immediately proximal and immediately distal, respectively, of the radiopaque marker;

said dimensionally reduced radiopaque marker at its said connected condition has a length substantially the same as the spiral ribbon length and overlays generally the entirety of the spiral ribbon; and whereby the flexibility of the pusher component is minimally impacted by the radiopaque marker at its connected condition.

2. The system of claim 1, wherein said radiopaque marker defines an arc greater than 180°.

3. The system of claim 1, wherein the radiopaque marker is substantially tubular and encircles at least a portion of said spiral ribbon.

4. The system of claim 1, wherein said radiopaque marker is a crimped marker, said outer surface thereof as thus assembled onto the spiral ribbon having been dimensionally reduced by crimping from the pre-assembly radiopaque marker.

* * * * *